United States Patent
Hovland et al.

(10) Patent No.: US 9,909,995 B2
(45) Date of Patent: Mar. 6, 2018

(54) INSPECTION TOOL

(71) Applicant: Vision IO AS, Stavanger (NO)

(72) Inventors: Øyvind Hovland, Røyneberg (NO); André Hognestad, Randaberg (NO)

(73) Assignee: Vision IO AS, Stavanger (NO)

( * ) Notice: Subject to any disclaimer, the term of this patent is extended or adjusted under 35 U.S.C. 154(b) by 0 days.

(21) Appl. No.: 15/303,913

(22) PCT Filed: Apr. 16, 2015

(86) PCT No.: PCT/EP2015/058286
§ 371 (c)(1),
(2) Date: Oct. 13, 2016

(87) PCT Pub. No.: WO2015/158837
PCT Pub. Date: Oct. 22, 2015

(65) Prior Publication Data
US 2017/0038310 A1    Feb. 9, 2017

(30) Foreign Application Priority Data
Apr. 16, 2014 (NO) .................................. 20140514

(51) Int. Cl.
*G01N 21/00*    (2006.01)
*G01N 21/954*    (2006.01)
(Continued)

(52) U.S. Cl.
CPC ......... *G01N 21/954* (2013.01); *E21B 36/001* (2013.01); *E21B 47/0002* (2013.01);
(Continued)

(58) Field of Classification Search
CPC ........ G01N 33/2823; G01N 9/36; G01N 1/12; G01N 21/3504; G01N 25/04; G01N 7/00;
(Continued)

(56) References Cited

U.S. PATENT DOCUMENTS 5,090,259 A    2/1992    Shishido et al.
5,519,543 A    5/1996    Olsson et al.
(Continued)

FOREIGN PATENT DOCUMENTS

GB    2293513 A    3/1996
GB    2491577 A    12/2012
(Continued)

OTHER PUBLICATIONS

International Search Report and Written Opinion dated May 20, 2015 for International Application Serial No. PCT/EP2015/058286, International Filing Date: Apr. 16, 2015, consisting of 14 pages.
(Continued)

*Primary Examiner* — Michael P Stafira
(74) *Attorney, Agent, or Firm* — Christopher & Weisberg, P.A.

(57) ABSTRACT

An inspection tool for inspecting oil and/or gas production and/or injection wells and pipes is provided. The tool comprises at least an image sensor, one or more processors or chips and one or more power supplies. The tool further comprises at least a first and a second chamber being insulated from each other. The first chamber comprises the image sensor and is provided with one or more passive cooling means, and the second chamber comprises the one or more processors and is provided with one or more active cooling means. Further, a method for cooling such inspection tool is provided.

9 Claims, 2 Drawing Sheets

Figure 1:
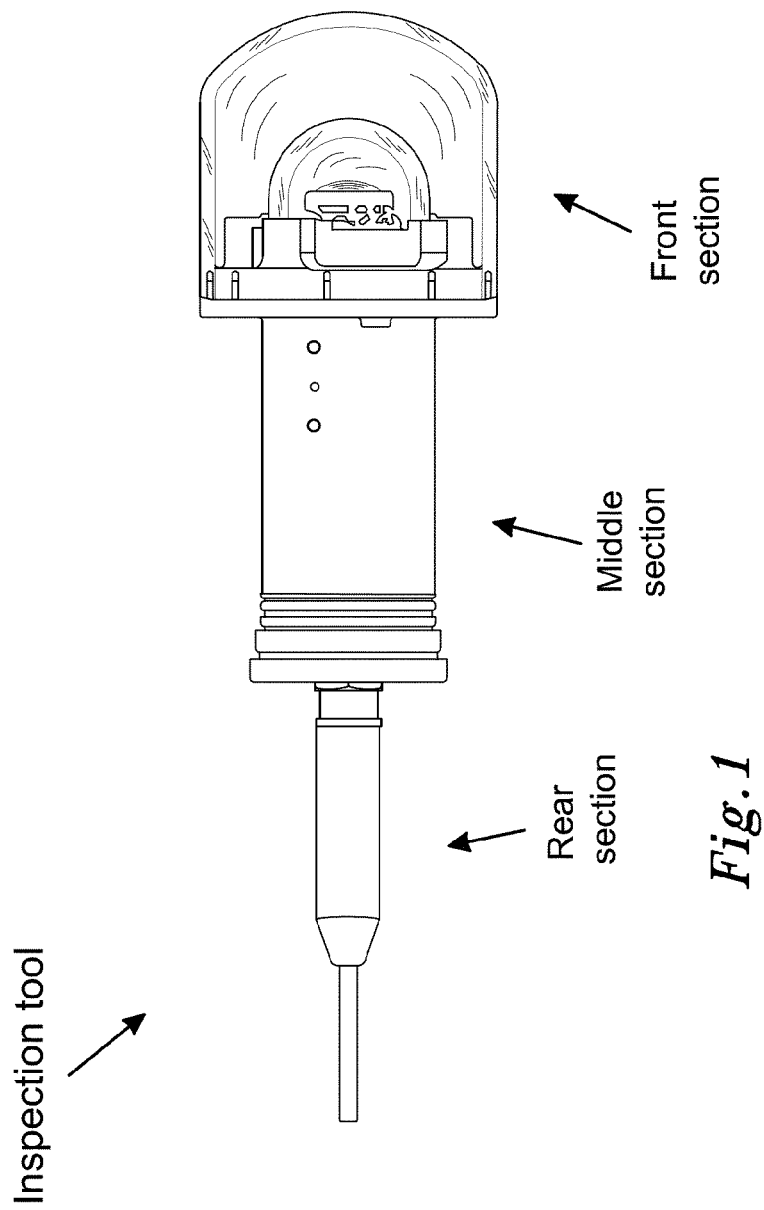

(51) Int. Cl.
*E21B 47/00* (2012.01)
*G01M 3/00* (2006.01)
*G02B 23/24* (2006.01)
*E21B 36/00* (2006.01)
*G01M 5/00* (2006.01)
*G01N 17/04* (2006.01)

(52) U.S. Cl.
CPC .......... *G01M 3/005* (2013.01); *G01M 5/0033* (2013.01); *G01M 5/0075* (2013.01); *G01N 17/04* (2013.01); *G02B 23/24* (2013.01); *G02B 23/2484* (2013.01); *G02B 23/2492* (2013.01); *G01N 2021/9542* (2013.01); *G01N 2201/0231* (2013.01)

(58) Field of Classification Search
CPC .... G01N 17/04; G01N 1/14; G01N 2021/651; G01N 2021/9542; G01N 21/31; G01N 21/65; G01N 21/954; G01N 2201/0231
See application file for complete search history.

(56) References Cited

U.S. PATENT DOCUMENTS

| | | | |
|---|---|---|---|
| 5,931,000 A | 8/1999 | Turner et al. | |
| 6,580,449 B1 | 6/2003 | Meltzer | |
| 7,671,983 B2 * | 3/2010 | Shammai | E21B 49/081 356/301 |
| 8,138,471 B1 | 3/2012 | Shedlock et al. | |
| 2004/0211894 A1 | 10/2004 | Hother et al. | |
| 2005/0104176 A1 | 5/2005 | Rodney et al. | |
| 2007/0119244 A1 * | 5/2007 | Goodwin | E21B 47/10 73/152.28 |
| 2009/0008560 A1 * | 1/2009 | Gunn | G01N 21/3504 250/343 |
| 2011/0087434 A1 | 4/2011 | Lie | |
| 2012/0192640 A1 | 8/2012 | Minh et al. | |

FOREIGN PATENT DOCUMENTS

| | | |
|---|---|---|
| GB | 2500671 A | 10/2013 |
| WO | 2013/144557 A2 | 10/2013 |

OTHER PUBLICATIONS

Norweigan Search Report dated Sep. 30, 2014 for corresponding Norwegian Application Serial No. 20140514, Norwegian Filing Date: Apr. 16, 2014, consisting of 2 pages.

* cited by examiner

INSPECTION TOOL

CROSS-REFERENCE TO RELATED APPLICATIONS

This application is a Submission under 35 U.S.C. § 371 for U.S. National Stage Patent Application of, and claims priority to, International Application Number PCT/EP2015/058286, filed Apr. 16, 2015, entitled "AN INSPECTION TOOL", which is related to and claims priority to Norwegian Patent Application Number 20140514, filed Apr. 16, 2014, the entire contents of both of which are hereby incorporated herein by reference.

TECHNICAL FIELD

Embodiments herein relate to an inspection tool for inspecting oil and/or gas wells and pipes.

BACKGROUND

In the drilling and production of oil and gas wells, it is often necessary to obtain inner surface information concerning conditions present within the borehole. For example, tools and other objects may become lodged in the borehole during the drilling of a well. Such objects must be retrieved before drilling can continue.

In the operation and/or periodic maintenance of producing or injection wells, it is frequently necessary to obtain information about the construction and/or operating condition of production equipment located downhole. For example, detection of the onset of corrosion damage to well tubing or casing within a borehole enables the application of anti-corrosive treatments to the well. Early treatment of corrosive well conditions prevents the highly expensive and dangerous replacement of corrosion damaged well production components.

For performing other maintenance operations in a production well environment, such as replacement of various flow control valves or the inspection of the location and condition of casing perforations, it is highly desirable for an operator located at the surface to obtain accurate, real-time information about downhole conditions.

In fact, new regulations require operators of oilfields to perform a visual inspection of their safety/barrier valves after certain operations to verify cleanness in order to secure a further safe operation. These are often referred to as BlowOut Preventers (BOP) which are large, specialized valves or similar mechanical devices, usually installed redundantly in stacks, used to seal, control and monitor oil and gas wells, and intended to prevent tubing (e.g. drill pipe and well casing), tools and drilling fluid from being blown out of the wellbore (also known as borehole, the hole leading to the reservoir) when a blowout threatens.

Other tubulars may need inspection. This is the case of risers, large tubulars connecting Oil and Gas exploration or production platforms or ships to subsea installations.

Visual inspection involves inserting an apparatus with sensors into the pipe and lowering it towards the oil and/or gas reservoir. The apparatus is a camera tool adjusted for visual inspection. The sensors build into the tool apparatus may also measure temperature, pressure or other variables of interest. In combination with the depth may these values be plotted graphically and can be compared to other graphs of an ideal or wanted case in order to evaluate the condition of the pipe.

Introducing inspection tools with extended sensor capabilities however also mean introducing hardware that generates heat into the pipes, for example camera chips, processors, batteries and lighting means. Due to the pressure in the well and other factors, high temperatures may be present in the environment were the apparatus is inserted. These temperatures are usually up to 150 degrees Celsius, but can reach an excess of 300 degrees Celsius. The hardware within the device that generates heat is sensible to high temperatures. As a consequence, inserting the apparatus in the well pipe may heat up the apparatus both externally and internally to a critical temperature, giving a threshold for how long the device can be placed in the well pipe without causing damage to the hardware. This means that the hardware necessary for performing inspection of the well needs to be cooled to be able to extend the threshold value and thus the working time to be as long as possible and thereby enable a complete inspection to be performed.

However, not all the hardware installed in an inspection tool has the same sensitivity towards high temperatures. For example, power supply, camera optics and sensors are way more temperature tolerant than processors, chips and camera electronics, even if the last mentioned devices are the one producing the most heat during operation.

As more and more active components and electronics are introduced in inspection tools, the need for cooling is increasing. This is in prior art done by passive cooling, employing combinations of heat insulating and reflecting materials in combination with storage materials, separating into separate chambers and vacuum to extend this timeframe. However, this does not provide sufficient cooling for fully equipped inspection tools.

It is therefore a need for a new cooling assembly for inspection tools with heat generating components installed operating in high pressure environments.

SUMMARY

One object of the disclosure is to reduce or ameliorate at least one of the disadvantages of the prior art systems and/or methods, or to provide a useful alternative. This object is achieved by an inspection tool for inspecting oil and/or gas production and/or injection wells and pipes at least comprising an image sensor, one or more processors or chips and one or more power supplies. The tool comprises at least a first and a second chamber being insulated from each other. The first chamber comprises the image sensor and is provided with one or more passive cooling means, and the second chamber comprises the one or more processors and is provided with one or more active cooling means.

Optionally, the inspection tool may comprise a third chamber being insulated from the first chamber and from the second chamber. The third chamber may comprise the one or more power supplies and may be provided with one or more passive cooling means.

Optionally, the first chamber may provide a front section, the second chamber may provide a middle section and the third chamber may provide a rear section of the inspection tool.

Optionally, the front, middle and rear section, respectively, may be arranged to be independently removed from the rest of the inspection tool.

Optionally, the one or more active cooling means may be one or more Peltier thermoelectric cooling devices.

Optionally, the one or more passive cooling means may comprise heat insulating, reflecting and/or storing materials.

According to a second aspect of embodiments herein, the object is achieved by a method for cooling an inspection tool for inspection of oil and/or gas production and/or injection wells and pipes. The tool at least comprises an image sensor, one or more processors or chips and one or more power supplies, and at least a first and a second chamber being insulated from each other. The first chamber comprises the image sensor, and the second chamber comprises the one or more processors. The inspection tool is adapted to cool the first chamber by one or more passive cooling means, and to cool the second chamber by one or more active cooling means.

FIGURES

Figure 2:
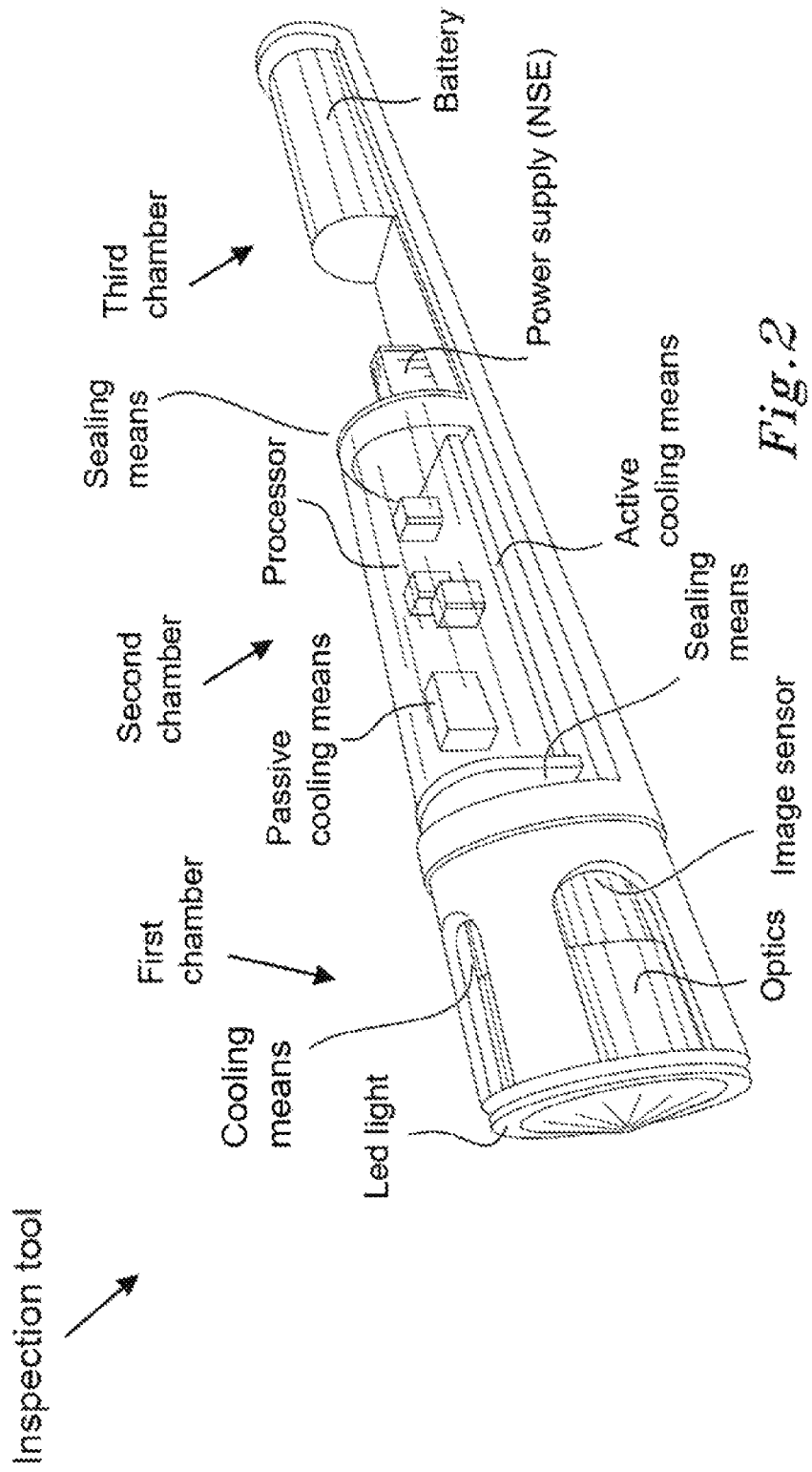

FIG. 1 illustrates an example of an inspection tool for fluid filled pipes according to state of the art, FIG. 2 illustrates an example of an embodiment comprising three chambers over which the components of the inspection tool are distributed.

DETAILED DESCRIPTION

In the following, embodiments herein will be discussed and example embodiments will be described by referring to the accompanying drawings.

Embodiments herein relate to an inspection tool and to methods for cooling an inspection tool for well pipes in use in the oil and gas industry. An inspection tool for inspecting oil and/or gas production and/or injection wells and pipes will now be described.

The inspection tool may comprise at least a first and a second chamber being insulated from each other. The first chamber comprises the image sensor and is provided with one or more passive cooling means, and the second chamber comprises the one or more processors and is provided with one or more active cooling means. The inspection tool may comprise a third chamber being insulated from the first chamber and from the second chamber. The third chamber may comprise one or more power supplies and may be provided with one or more passive cooling means. The first chamber may provide a front section, the second chamber may provide a middle section and the third chamber may provide a rear section of the inspection tool.

In the following, an inspection tool comprising three separate chambers connected to one another will be exemplified. The chambers are separated from one another by airtight sealing means and heat isolating means. The chambers are further shielded against the outer environment by heat isolating or storing materials placed in the cavity of the assembly. The three chambers are further separated from the surrounding environment by a capsule.

The inspection tool at least comprises an image sensor, one or more processors or chips and one or more power supplies. The internal hardware may be cooled with both passive and active cooling means. As an example, the passive cooling means may be heat insulating, reflecting and/or storing materials. As a further example, the active cooling means may comprise at least one Peltier thermoelectric cooling unit, placed in contact with the heat generating components. The active cooling means may further be in contact with material enabling heat transfer and storage of the internal components, like e.g. materials introduced in the assembly and/or the capsule.

FIG. 2 is an illustration of one example. It shows an inspection tool comprising three separate chambers being separated from one another via sealing means that generate an air tight seal between the chambers when the capsule is in place. The sealing means also shield the chambers terminally. It may further comprise several passive cooling means. As an example this may be heat insulating, reflecting and/or storing materials. The inspection tool may further comprise one or several active cooling means. As an example such active cooling means may be a Peltier thermoelectric cooling unit.

In the example embodiment, the front chamber of the assembly may comprise camera sensor, optical means and lighting means. The camera means may be a CMOS camera chip. The lighting means may be a LED lighting source. The camera sensor may be cooled by both active and passive cooling means. In the example embodiment illustrated in FIG. 2, the front chamber is only cooled by passive cooling means. The passive cooling means may be heat insulating, reflecting and/or storing materials.

In the example embodiment of FIG. 2, the middle chamber comprises the camera electronics, which may include processors and chips, which as already mentioned are the most temperature sensitive components of the inspection tool, however also generating heat in operation. The processor may be an FPGA processor.

The inspection tool may be adapted to cool the first chamber by one or more passive cooling means, and to cool the second chamber by one or more active cooling means.

According to the example embodiment illustrated in FIG. 2, alternatively the middle chamber in an inspection tool comprising three chambers may comprise both passive and active cooling means. The passive cooling means may be heat insulating, reflecting and/or storing materials. The active cooling means does however contribute most to the cooling, and are in this example placed so that heat is removed from the processing means and stored in a heat storing material. As an example, the active cooling means may be placed in contact with the processing means and in contact with heat storing means, for example heat storing material. In an example of the embodiment illustrated in FIG. 2, the active cooling means may be Peltier thermoelectric cooling devices.

The Peltier thermoelectric cooling devices (thermoelectric cooling—TEC) are employed in a wide arrange of domestic products as for example in portable coolers. A Peltier thermoelectric cooling device is a solid state active heat exchanger. The cooling device is built up of at least two semiconductors, one n-type and one p-type, that are placed in parallel to each other and joined together with a thermally conductive plate on top and below. Applying a DC current to the semiconductors creates a temperature difference, causing the side with the cooling plate to absorb heat and to move (through to) towards the side with the heat sink. The cooling ability of the total unit is in proportion to the number of semiconductors in it, and due to recent advances in the semiconductor industry, it is now possible to include a sufficient number of elements in one unit to be included in an inspection tool. A Peltier thermoelectric cooling device will typically have a maximum temperature difference of 60-70° C. between the hot and cold side.

The active cooling means may also be a liquid cooled element or a fan cooled element.

In the example embodiment of FIG. 2, the rear chamber incorporates power supply means and communication means. The power supply means may for example be a power supply device and a battery. The communication means may be altered after need and may for example be fiber optics, communication cable and/or storage means.

The three chambers of the inspection tool described above may preferably be thermally and mechanically insulated from each other. In one embodiment, this is achieved by providing vacuum in at least one of the first and second chamber, e.g. by means of a valve into the respective chamber on which a vacuum pump can be connected.

Hence, there are three different heat environments to deal with that do not significantly influence each other, and that may be cooled differently according to the temperature requirements and heat production connected to the components in each respective chamber. The front, middle and rear section, respectively, may be arranged to be independently removed from the rest of the inspection tool. Thus, each chamber may individually be replaced or removed for maintenance.

The above description discloses different example embodiments for illustrative purposes. A person skilled in the art would realize a variety of chambers, chamber components and cooling means within the scope of the appended claims.

The invention claimed is:

1. An inspection tool for inspecting at least one of oil gas production and injection wells and pipes, the inspection tool comprising:
    at least one of at least one processor and at least one chip, and at least one power supply;
    at least a first and at least a second chamber being insulated from each other and a sealing means configured for generating an air tight seal between the first chamber and the second chamber, the first chamber being separated from the second chamber with the sealing means, the first chamber comprising the image sensor and being provided with at least one passive cooling means configured for being in contact with material enabling heat transfer and storage of the internal components; and
    the second chamber comprising at least one processor and being provided with at least one active cooling means configured for being in contact with material enabling heat transfer and storage of the internal components.

2. The inspection tool according to claim 1, further comprising a third chamber insulated from the first chamber and from the second chamber, the third chamber including the at least one power supply and being provided with at least one passive cooling means.

3. The inspection tool according to claim 2, wherein the first chamber provides a front section of the inspection tool, the second chamber provides a middle section of the inspection tool and the third chamber provides a rear section of the inspection tool.

4. The inspection tool according to claim 3, wherein each of the front, middle, and rear section is arranged to be independently removed from the rest of the inspection tool.

5. The inspection tool according to claim 1, wherein the at least one active cooling means is at least one of a Petlier thermoelectric cooling device.

6. The inspection tool according claim 1, wherein the at least one passive cooling means comprises at least one of a heat insulating material, a reflecting material, and a storing material.

7. The inspection tool according to claim 1, further comprising a vacuum provision means adjusted to provide vacuum in at least one of the first and second chamber.

8. The inspection tool according to claim 1, wherein the first and the second chamber are cooled differently according to the temperature requirements and heat production connected to the components in each respective chamber.

9. A method for cooling an inspection tool for inspection of at least one of oil, gas production, injection wells and pipes, the tool including: an image sensor, at least one of at least one processor and at least one chip, and at least one power supply, at least a first chamber, a second chamber, and a sealing means configured for generating an air tight seal between the first chamber and the second chamber, the first chamber and the second chamber being insulated from each other and the first chamber being separated from the second chamber with the sealing means, the first chamber including the image sensor, and the second chamber including the at least one processor, the method comprising:
    cooling of the first chamber by at least one passive cooling means configured for being in contact with material enabling heat transfer and storage of the internal components; and
    cooling of the second chamber by at least one active cooling means configured for being in contact with material enabling heat transfer and storage of the internal components.

* * * * *